United States Patent [19]

Harris, Sr. et al.

[11] 4,044,616
[45] Aug. 30, 1977

[54] AUTOMATIC FLUID INJECTOR

[76] Inventors: Rano J. Harris, Sr., 1945 Carolyn Sue Drive; Rano J. Harris, Jr., 5443 Stonewall Drive, both of Baton Rouge, La. 70815; Julius P. Averette, Jr., 4332 Delaware St., Baton Rouge, La. 70805

[21] Appl. No.: 749,804

[22] Filed: Dec. 13, 1976

Related U.S. Application Data

[63] Continuation-in-part of Ser. No. 618,374, Oct. 1, 1975, Pat. No. 4,000,654.

[51] Int. Cl.$^2$ .............................................. G01N 1/12
[52] U.S. Cl. ............................ 73/422 GC; 73/423 A
[58] Field of Search ............ 73/422 GC, 423 A, 425.6

[56] References Cited

U.S. PATENT DOCUMENTS

| | | | |
|---|---|---|---|
| 3,552,212 | 1/1971 | Ohlin | 73/423 A |
| 4,000,654 | 1/1977 | Harris, Jr. | 73/423 A |

FOREIGN PATENT DOCUMENTS

| | | | |
|---|---|---|---|
| 1,209,182 | 10/1970 | United Kingdom | 73/423 A |

*Primary Examiner*—S. Clement Swisher
*Attorney, Agent, or Firm*—Llewellyn & Proctor

[57] ABSTRACT

An automatic fluid injector for accurately injecting preselected quantities of fluid specimens into an inlet of analytical instrument. The overall combination includes (a) the fluid injector sub-assembly, (b) an injector feed assembly for automatically continuously purging, cleaning and filling the barrel of said fluid injector sub-assembly and (c) a magazine, or feed tray, for transporting one or a plurality of vials of fluid specimens to the injector feed assembly for pick-up of the fluid specimen, and delivery to the barrel of said fluid injector sub-assembly. A feature of the invention is that fluid specimen can be passed from the extreme rearward end of the barrel of the fluid injector sub-assembly, entirely through the barrel and needle to purge, clean and remove contaminants as from previous specimens. Another feature is that the fluid specimen is ejected from the fluid injector sub-assembly, on closure of the valve thereof, by the forward movement of the barrel relative to the needle such that the needle moves rearwardly into the barrel to displace and eject fluid specimen through the dispensing end of the needle. An accurately measured fluid specimen is trapped on closure of the valve, after adequate flow through to remove contaminants, the amount of fluid specimen to be injected being predetermined by the preset volume to be displaced from the barrel by the extent of its forward movement which moves the rearward end of the needle into the barrel.

10 Claims, 12 Drawing Figures

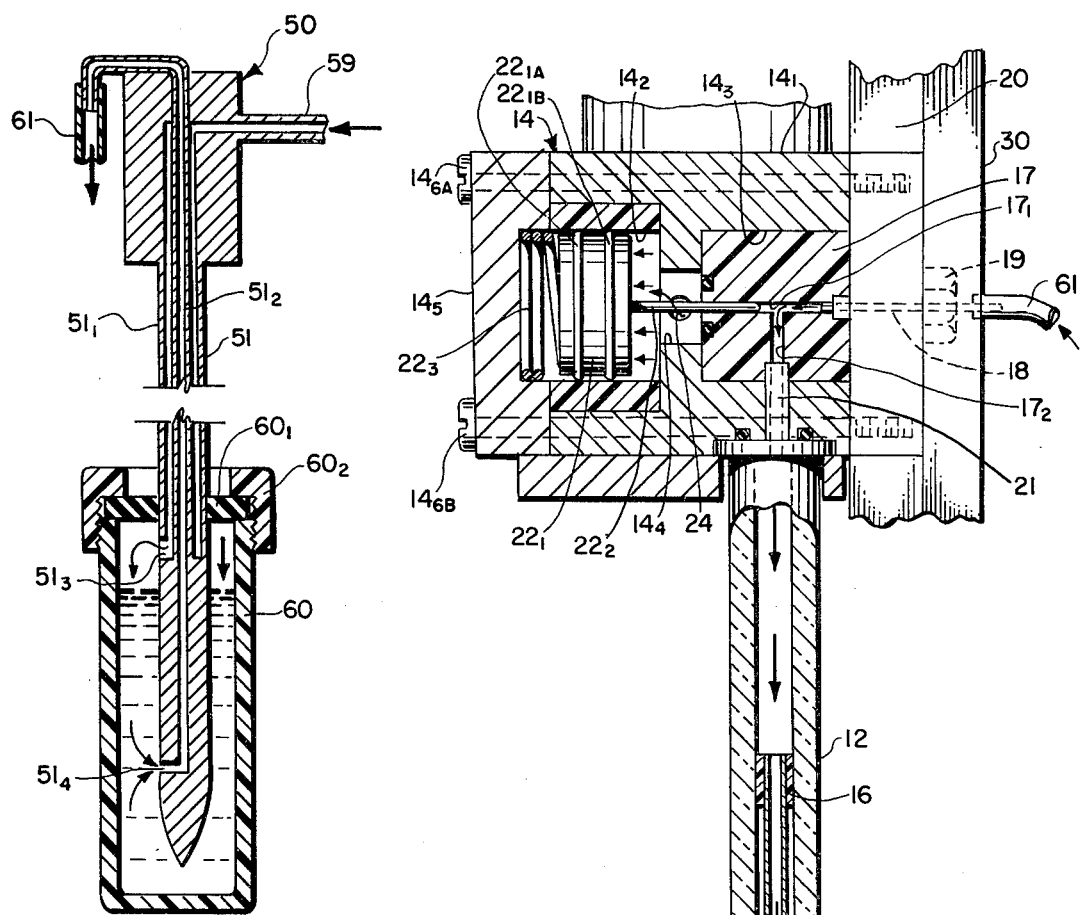
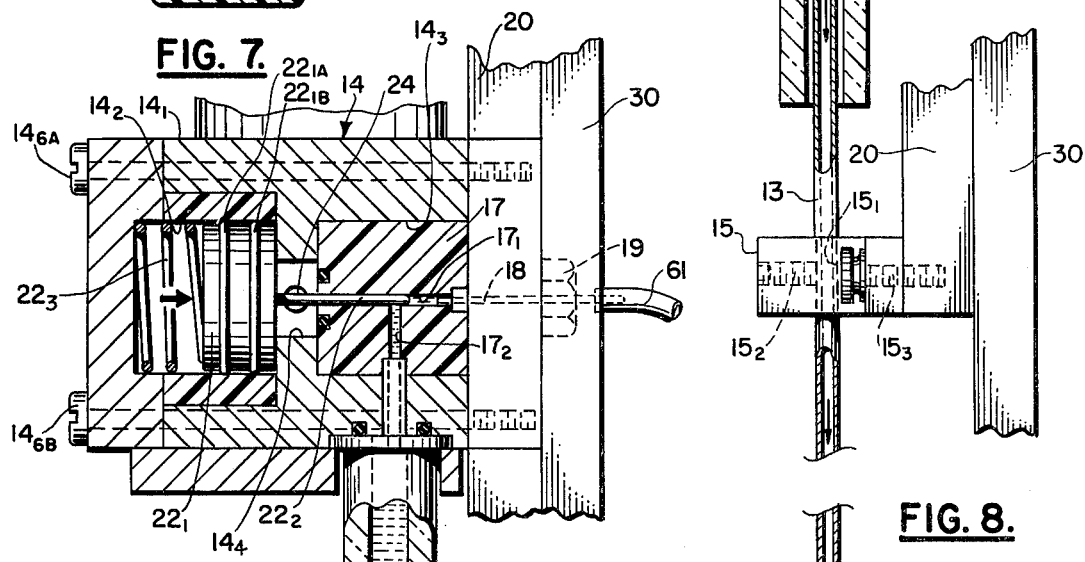
FIG. 7.
FIG. 8.
FIG. 9.

AUTOMATIC FLUID INJECTOR

RELATED APPLICATIONS

This application is a continuation-in-part of application Ser. No. 618,374 filed Oct. 1, 1975 now U.S. Pat. No. 4,000,654. It is related to subject matter covered in U.S. Pat. Nos. 3,754,443; 3,824,859; 3,885,438 and 3,940,995. All of these disclosures, herein referred to, are herewith incorporated by reference.

The present invention relates generally to automatic fluid injectors, or apparatus, for automatically measuring and injecting accurately measured quantities of fluids. More particularly, it relates to apparatus, especially fluid injection devices, for continuous automatic measurement and injection of very small, accurately measured quantities of gas and liquid specimens into various media, e.g., modern analytical instruments such as mass spectrographs or gas chromatographs.

Fluid injection devices, particularly needle syringes, have gained wide acceptance by the industry, and by the scientific community, generally, for use in dispensing infinitesimally small, accurately measured fluid specimens, e.g., to modern analytical instruments such as mass spectrometers and gas chromatographs. Such syringes embody apparatus comprising a tubular body or barrel, on the forward end of which is fitted a hollow or tubular needle and, at the opposite end, a slidable plunger which travels within the bore of the barrel. Syringes of such character, and related devices, are capable of dispensing very small fluid specimens, accurately measured, on the order of a few microliters, or very small fractions of a microliter, e.g., from about 0.01 to about 5 microliters, or fractional parts thereof.

In recent years, due to the obvious advantages offered by the combination of automatic fluid injection instruments, and modern data gathering techniques, which greatly reduce operating manpower without decrease in accuracy, there is considerable demand for improved automated devices of these types.

It is accordingly, a primary object of the present invention to provide new and novel fluid injectors readily adaptable to automatically perform the basic cyclic function of purging and cleaning, filling, and injecting.

A particular object is to provide apparatus capable of continuously cyclically serially withdrawing precisely measured, infinitesimally small quantities of gas or liquid specimens from prefilled vials or containers, injecting the specimens in seriatim in reproducible quantities, and cleaning prior to subsequent withdrawal and injection of a subsequent specimen.

A further object is to provide apparatus of simple and relatively inexpensive construction, particularly apparatus which can be readily serviced and operated, which apparatus readily lends itself to rapid mass production techniques.

Yet another object is to provide apparatus embodying further improvements over those devices specifically disclosed and claimed in application Ser. No. 618,374; and U.S. Pat. Nos. 3,754,443; 3,824,859; 3,885,438; and 3,940,995, supra.

These and other objects are achieved in accordance with the present invention which embodies improvements in fluid injector devices, notably automatic fluid injector systems. A preferred automatic fluid injector is one comprised of a barrel, or hollow tubular member, a hollow needle or cannula slidably mounted within the forward end of said barrel, and a valve located at the rearward end of said barrel for opening and closing the barrel to the flow of a fluid specimen therethrough from a suitable source. On opening the valve, the fluid specimen can be flowed through the barrel and needle to effectively clean these members and, on closure of the valve, a measured amount of the fluid specimen can be trapped inside the barrel and needle, and then on thrust of the dispensing end of the needle into a suitable media, e.g., the septum inlet to an analytical instrument, the fluid specimen can be injected by a relative forward movement of the barrel such that the needle moves rearwardly therewithin to displace and cause ejection of the fluid specimen through the dispensing end of the needle and into the inlet of the analytical instrument.

In its preferred aspects the needle, barrel and valve constitute a fluid injector sub-assembly which is mounted upon a plate to which the needle portion thereof is rigidly affixed, and the relative motion between the barrel and needle required in the ejection of an accurately measured portion of a fluid specimen is provided by means which produce motion of the barrel along a predetermined path as required for injection of a portion of the fluid specimen into an inlet to an analytical instrument. In a particularly preferred embodiment, the valve is physically incorporated or integrated within the rearward end of the barrel and provided with a stem which is actuable and movable, suitably by a piston unit, to open and close the valve to the flow of fluid specimen, and both the barrel and the valve are actuated and moved by a different means, suitably another piston unit, for providing the relative movement between the barrel and needle required in the injection of a fluid specimen. It is especially suitable that the plate, on which the fluid injector sub-assembly is mounted, be slidably mounted upon a base plate, and that the means which actuate the valve, and barrel, suitably a pair of piston units, be mounted upon the slide plate. Whereas yet another actuating and drive means, e.g., a piston unit, can be mounted upon the slide plate to effect movement and reciprocation of the barrel, and suitably the valve if integrated therewith, it is preferred to mount such means upon the base plate and thereby effect movement and reciprocation of the entire slide plate on which the fluid injector sub-assembly is mounted. Means are also provided for adjusting the relative distance of movement between the hollow needle and barrel of the fluid injector sub-assembly such that the rearward end of the needle moves a preselected distance into the barrel in displacing and ejecting fluid specimen from the barrel. A novel fluidic diversion valve is also employed to carry away the fluid specimen used for cleaning, purging and filling the fluid injector.

A particularly preferred type of automatic fluid injector is comprised of (a) a fluid injector sub-assembly inclusive of barrel and hollow needle slidably mounted therein, and valve for controlling the ingress of fluid specimen into the barrel and needle, (b) an injector feed assembly, or unit, for automatically purging, cleaning and filling the said fluid injector sub-assembly, and (c) a magazine, or feed tray, for transporting one or a plurality of fluid specimen containing vials and positioning same in relation to the injector feed assembly for pick-up of the fluid specimen, and delivery to the barrel and needle portions of the fluid injector sub-assembly. The automatic fluid injector is provided with automation or control means for repetitively and automatically carrying out the functions of cleaning, purging and filling the barrel and needle of the fluid injector sub-assembly with predetermined quantities of fluid specimens, in timed sequence, and the several sub-assemblies of the automatic fluid injector are generally contained within a housing, or housings. The sub-assemblies constituting (a) the feed injector sub-assembly, (b) the injector feed assembly, and (c) the magazine, or feed tray, are preferably contained within a single housing.

The injector feed assembly is constituted in part of a reciprocable hollow probe, or pair of hollow probes. In one aspect, a single hollow probe with upper and lower openings can be employed such that in a first timed sequence means are employed which pressurize the fluid contents of a vial after entry of the probe into the vial and, in a second times sequence, the same probe is repositioned and acts as a conduit for conveying the fluid contents of the vial to the barrel of the fluid injector sub-assembly as, e.g., in U.S. Pat. No. 3,754,443. In employing a pair of hollow probes, and these can be parallelly or concentrically mounted, one probe of the pair is generally employed to pressurize the contents of a vial, while the other serves as a conduit for pick-up of a fluid specimen from a vial delivered by the magnetic or feed tray, and as a medium for transport thereof to the fluid injector sub-assembly, as e.g., in Ser. No. 618,374. In either instance, means are thus provided which pressurize the fluid contents of a vial, and the fluid contents therefrom are conveyed via a conduit to the barrel of the fluid injector sub-assembly.

The barrel of the fluid injector sub-assembly is provided with a valved rearward opening, suitably one which can be opened or closed in desired sequence to permit egress of a fluid specimen from a vial via action of the injector feed assembly. On initial entry of a probe, or a pair of probes, into a vial, a portion of the fluid specimen thereof is normally passed into the rearward end of the barrel and flowed therethrough to the front thereof, thence through the needle. The fluid egresses through the dispensing end of the needle, this to clean and flush the barrel and needle of any contaminants. On closure of the valve the ingress of the fluid specimen is interrupted, as well as any egress of fluid specimen from the dispensing end of the needle. A fluid specimen, measured by the total volume of the barrel from its closed rearward end up to the rearward face of the needle projected therein plus the volume of the opening through the needle, is trapped within the barrel and needle. In such action, it is clear that when subsequently the dispensing end of the needle is inserted into an inlet to an analytical instrument and fluid specimen is injected therein, the amount of injected fluid specimen is predetermined and measured by that volume of the fluid specimen displaced by the forward movement of the barrel which causes the rearward end of the needle to move into the barrel and displce the fluid specimen. In calibration of the fluid injector sub-assembly, zero is usually taken as the cross-section at the very rearward end of the barrel. The volume between the rearward end of the barrel and the rearward face of the needle at the front of the barrel is set at a preselected distance to give the desired volume, and precision is obtained by moving the rearward face of the needle over the preset distance to flush with the extreme end of the closed barrel, i.e., the zero set point.

The characteristics of preferred automatic fluid injector, and the principle of its operation, will be more fully understood by reference to the following detailed description of preferred embodiments, and to the attached drawings to which reference is made in subsequent description. Similar numbers are used in the different figures to represent similar parts or components in different figures, and subscripts are used with numbers where there are duplicate components.

Figure 1:
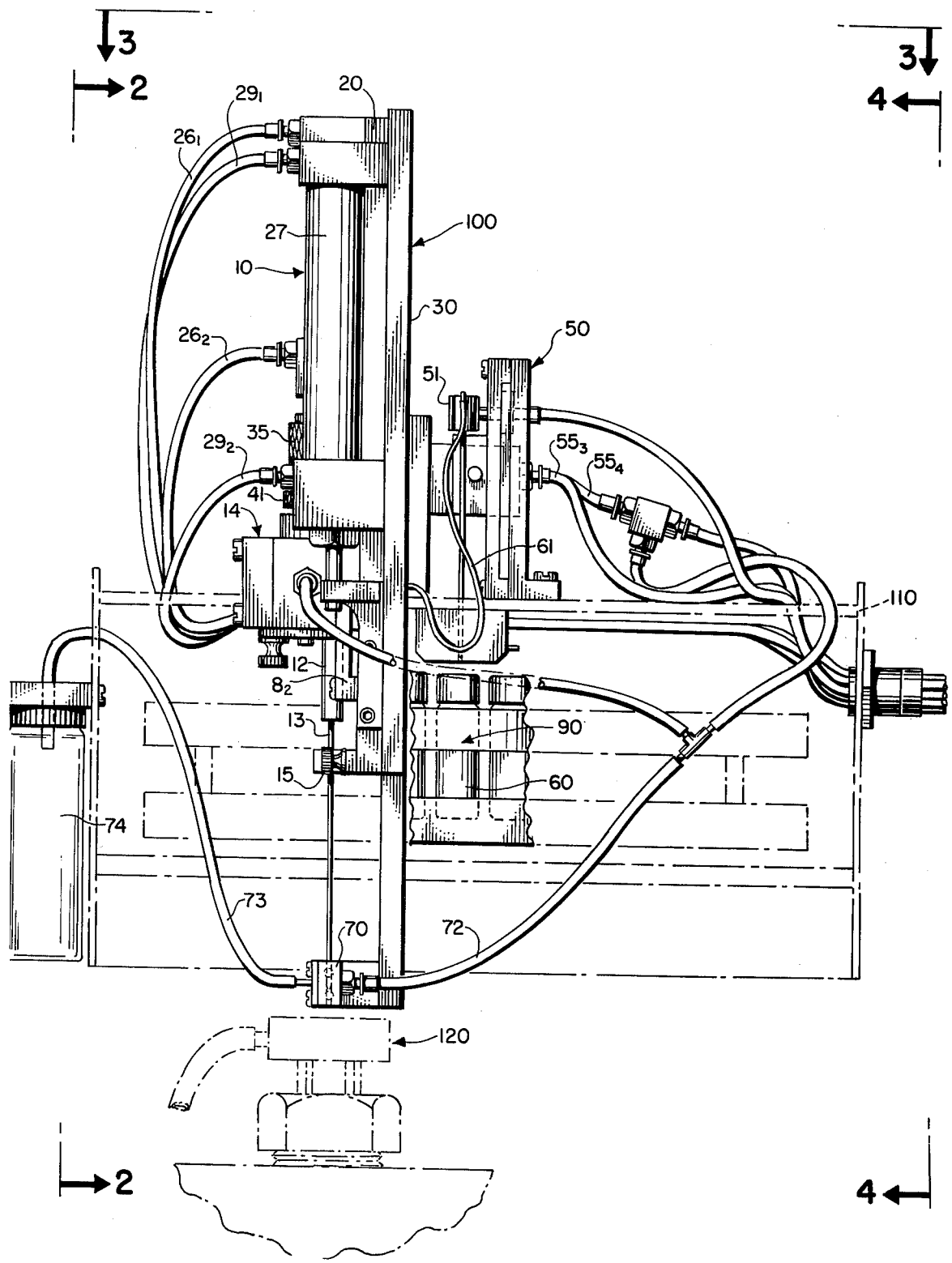
FIG. 1 depicts a front elevation view, in partial section, of a preferred automatic fluid injector wherein is included a housing which contains (a) a fluid injector sub-assembly, (b) an injector feed unit, inclusive of its probe assembly, and (c) a carrousel type magazine, or feed tray.
Figure 2:
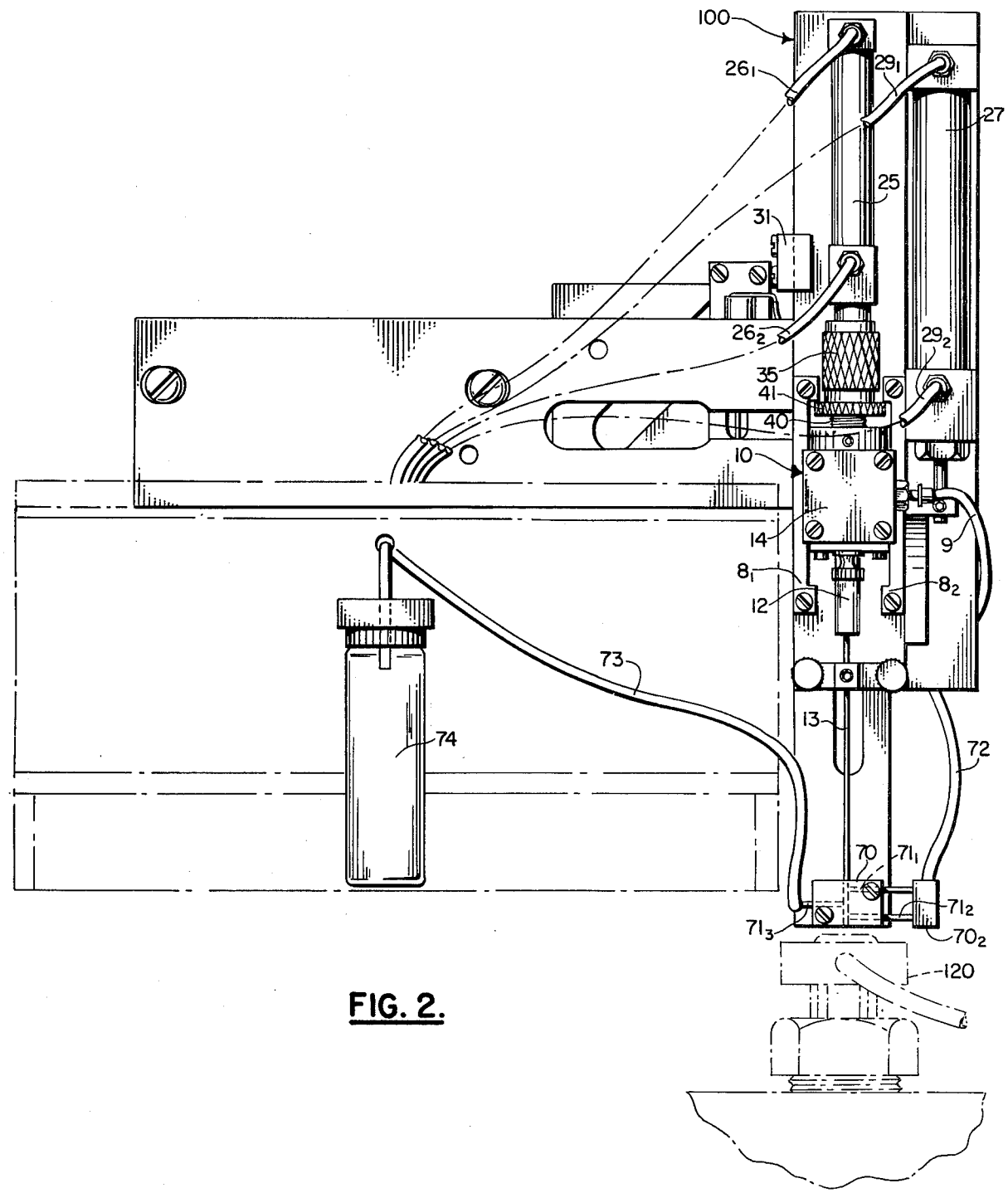
FIG. 2 depicts a left side elevation view of said automatic fluid injector, the view being taken along line 2—2 of the preceding figure.
Figure 3:
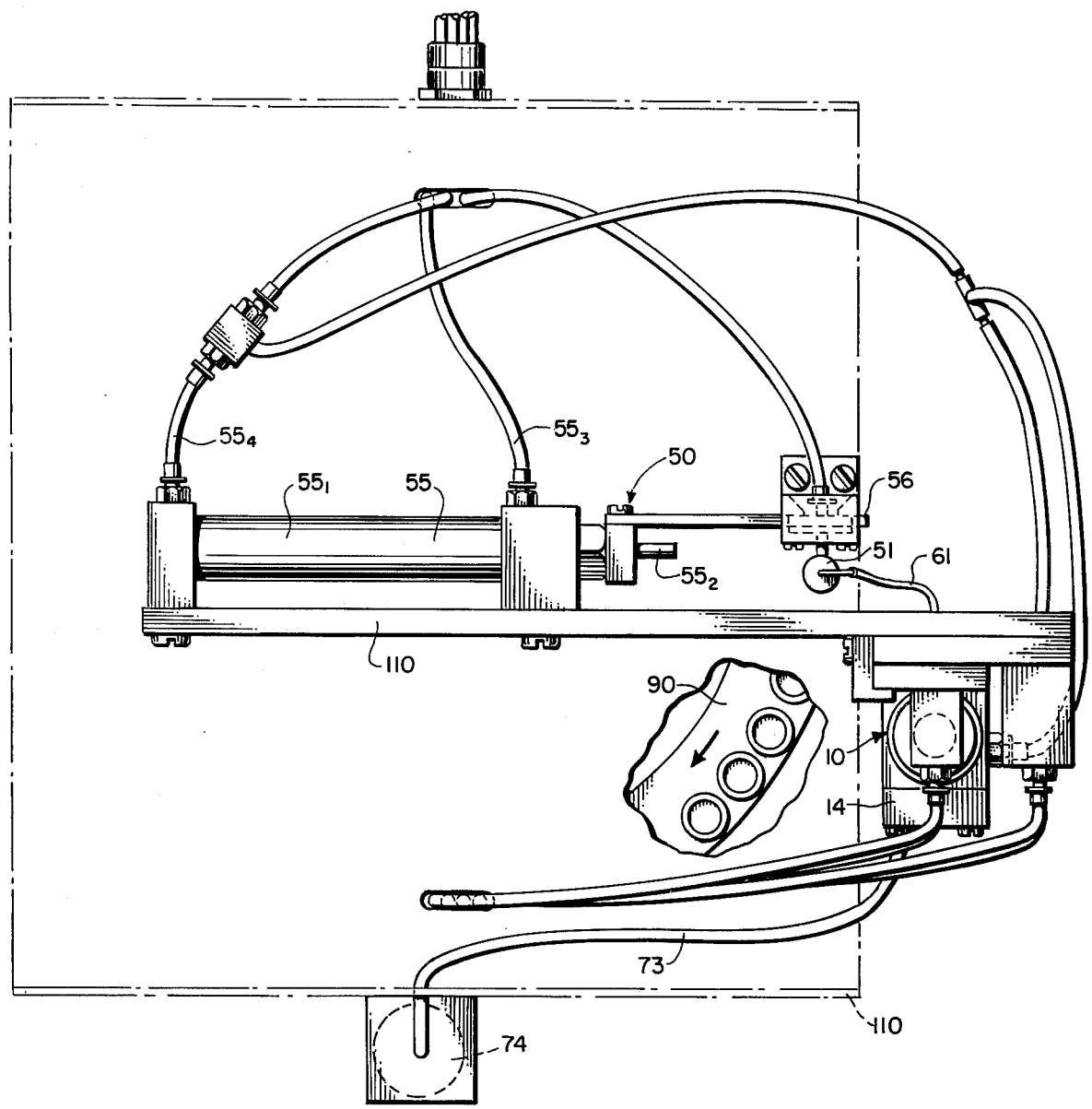
FIG. 3 depicts a top plan view of said automatic fluid injector, the view being taken along line 3—3 of FIG. 1.
Figure 4:
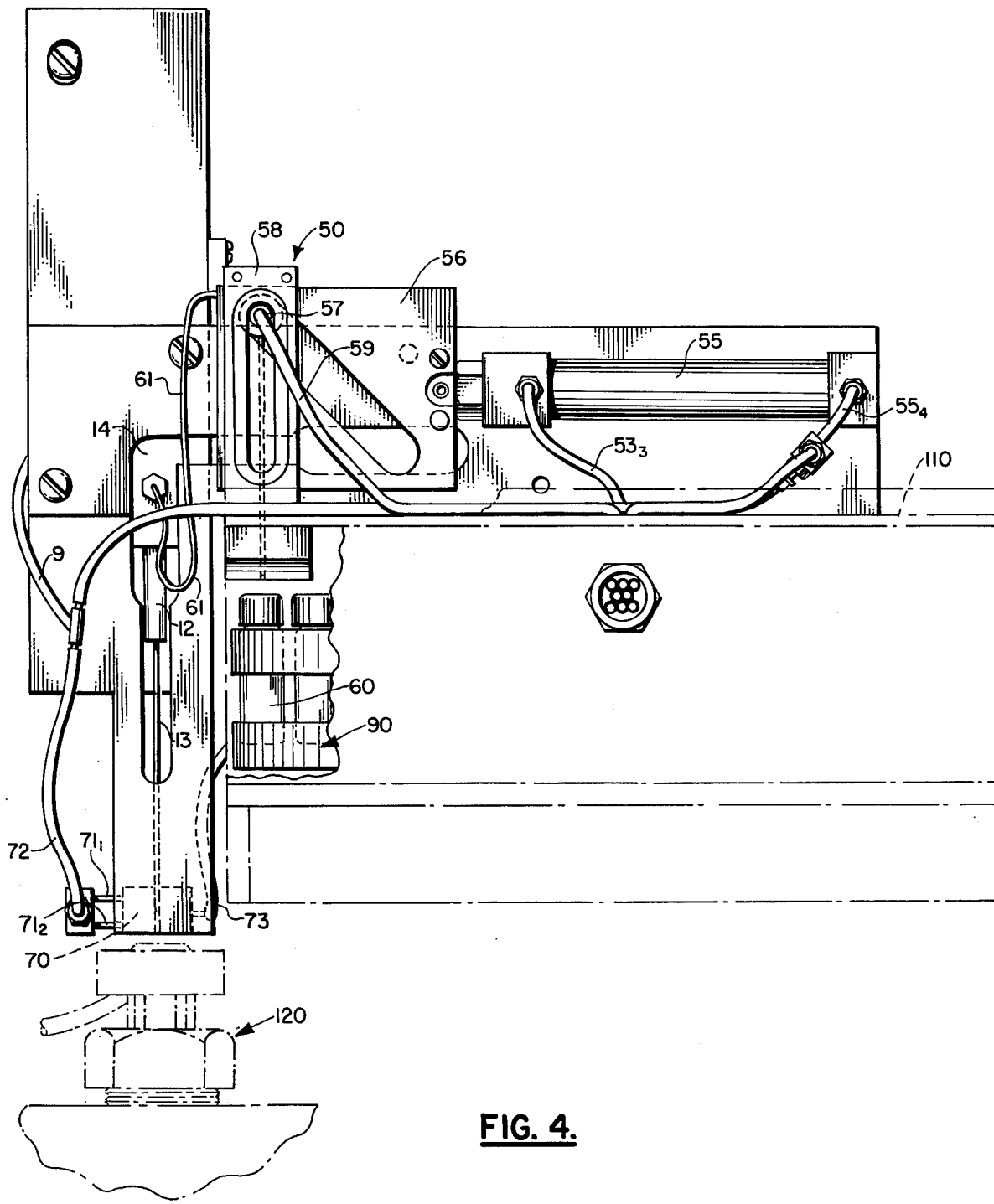
FIG. 4 depicts a right side elevation view of said automatic fluid injector, the view being taken along line 4—4 of FIG. 1.
Figure 5:
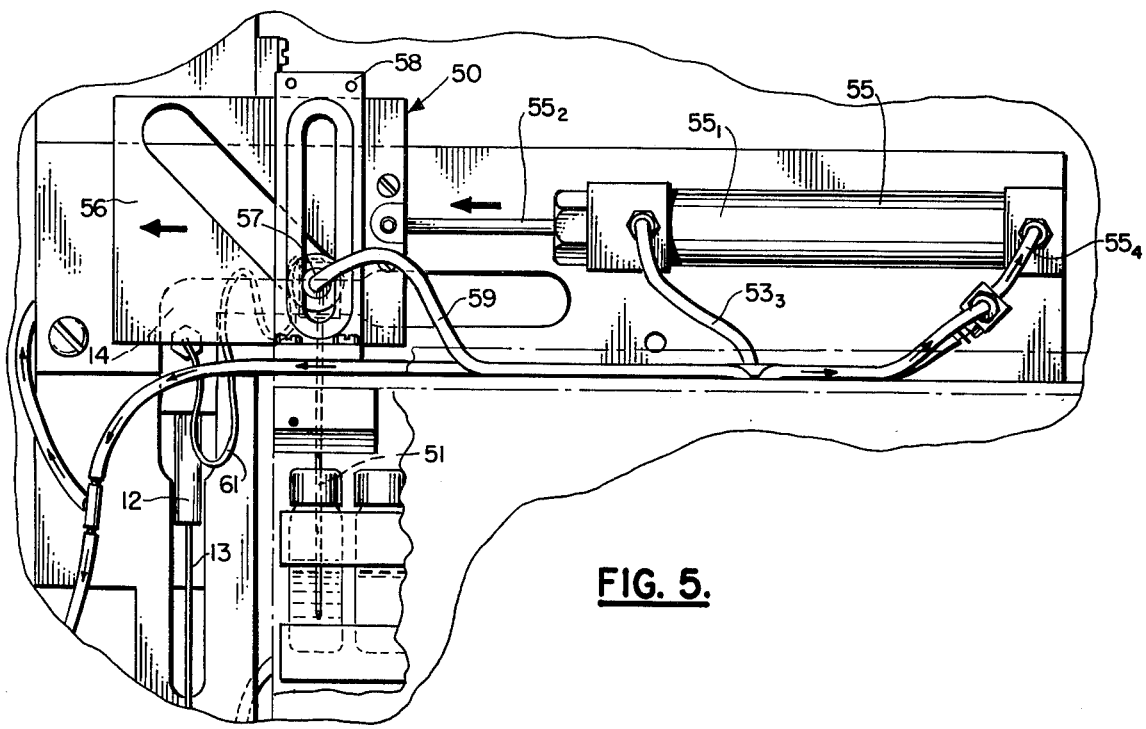
FIG. 5 depicts a side elevation view, illustrating in some further detail the operation of the injector feed unit in taking a fluid specimen from a filled vial delivered thereto by the magazine, or feed tray, and the operation and function of these units in delivery of the fluid specimen to the fluid injector sub-assembly.
Figure 6:
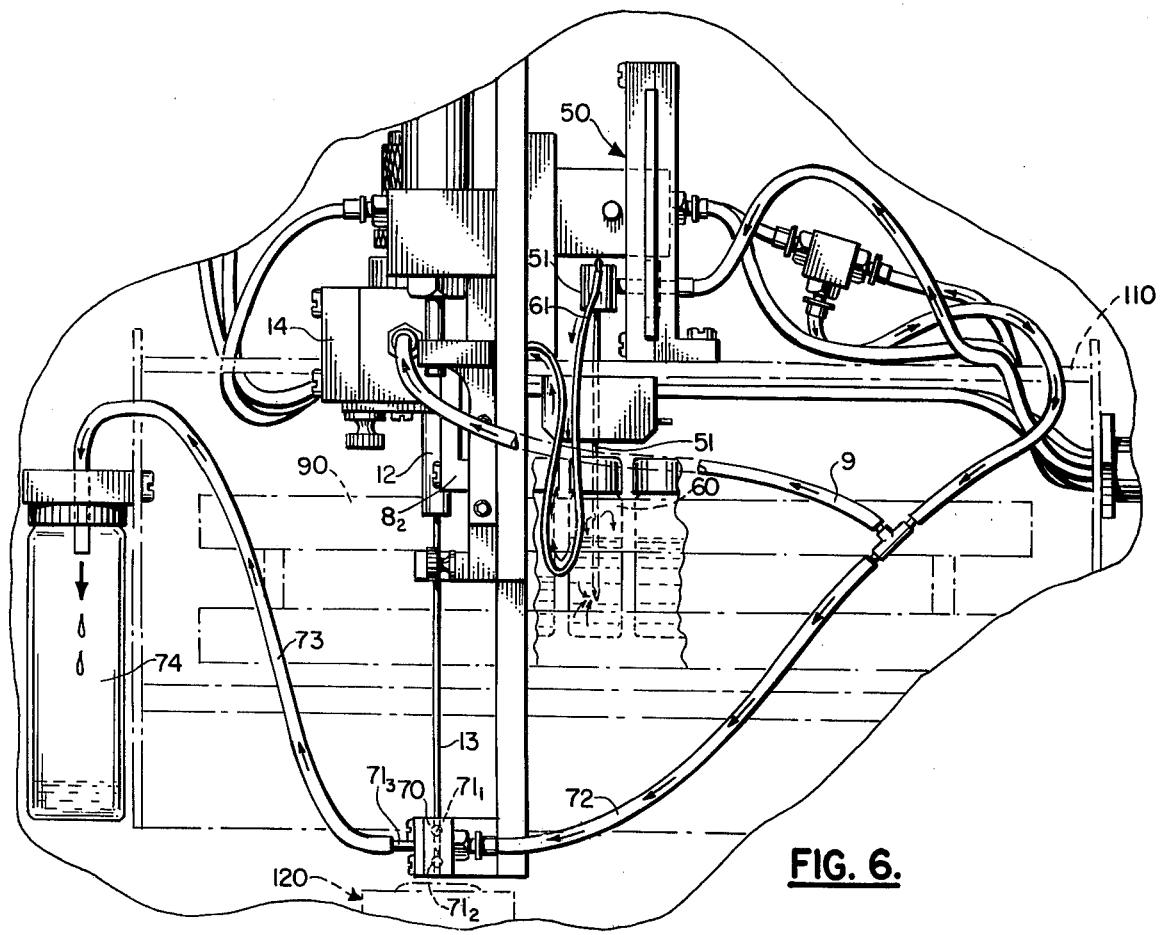

FIG. 6, taken in connection with FIG. 5, depicts in further detail the mechanism by virtue of which a fluid specimen is taken from a vial delivered by the magazine, or feed tray, and conveyed to the fluid injector sub-assembly.

FIG. 7 depicts in detail a preferred type of probe assembly for use in the pick-up, conveyance and delivery of a fluid specimen from a vial carried by the magazine, or feed tray.

FIG. 8 and 9 depict the principle or major components of the fluid injector sub-assembly and, taken together, define the functions of cleaning, purging and filling the fluid injector with a fluid specimen for injection.

Figure 10:
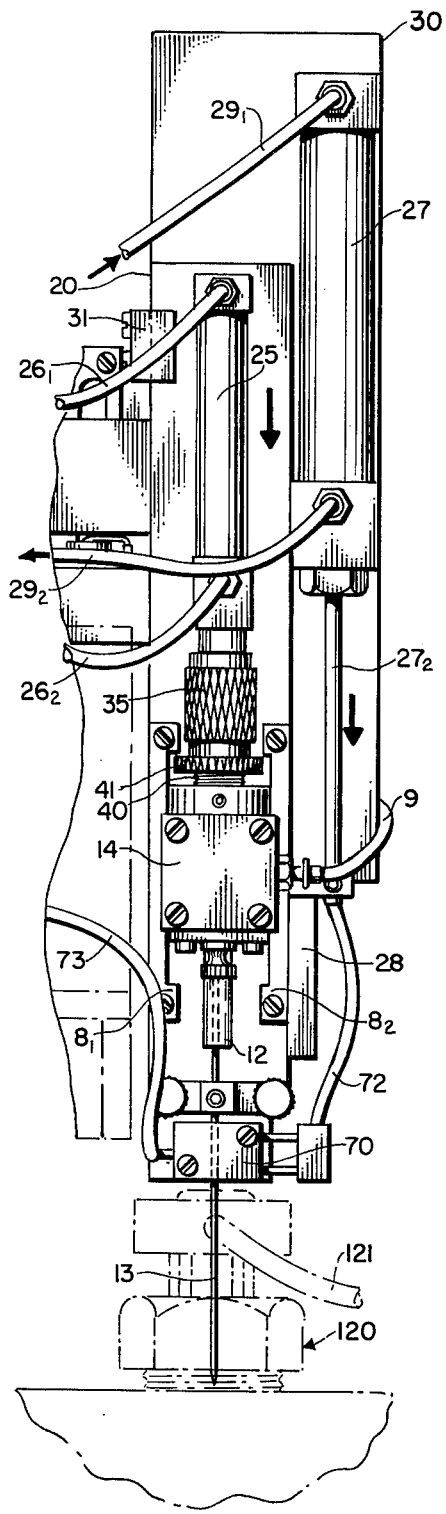
Figure 11:
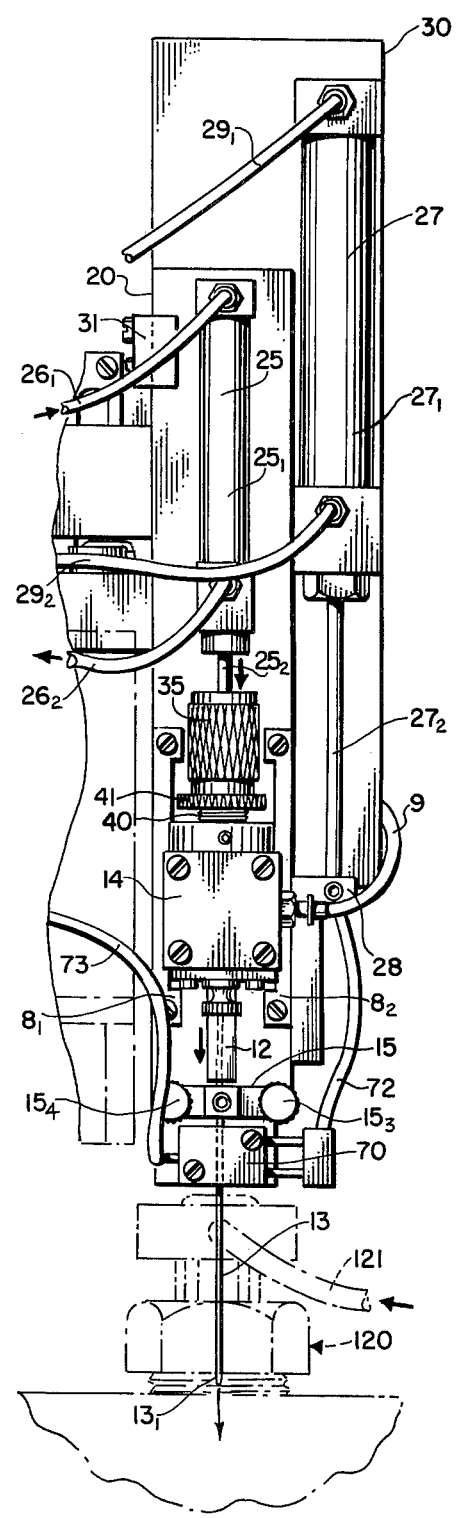

FIGS. 10 and 11 detail essentially the complete fluid injector sub-assembly and, taken together, define the function of injecting a fluid specimen.

Figure 12:
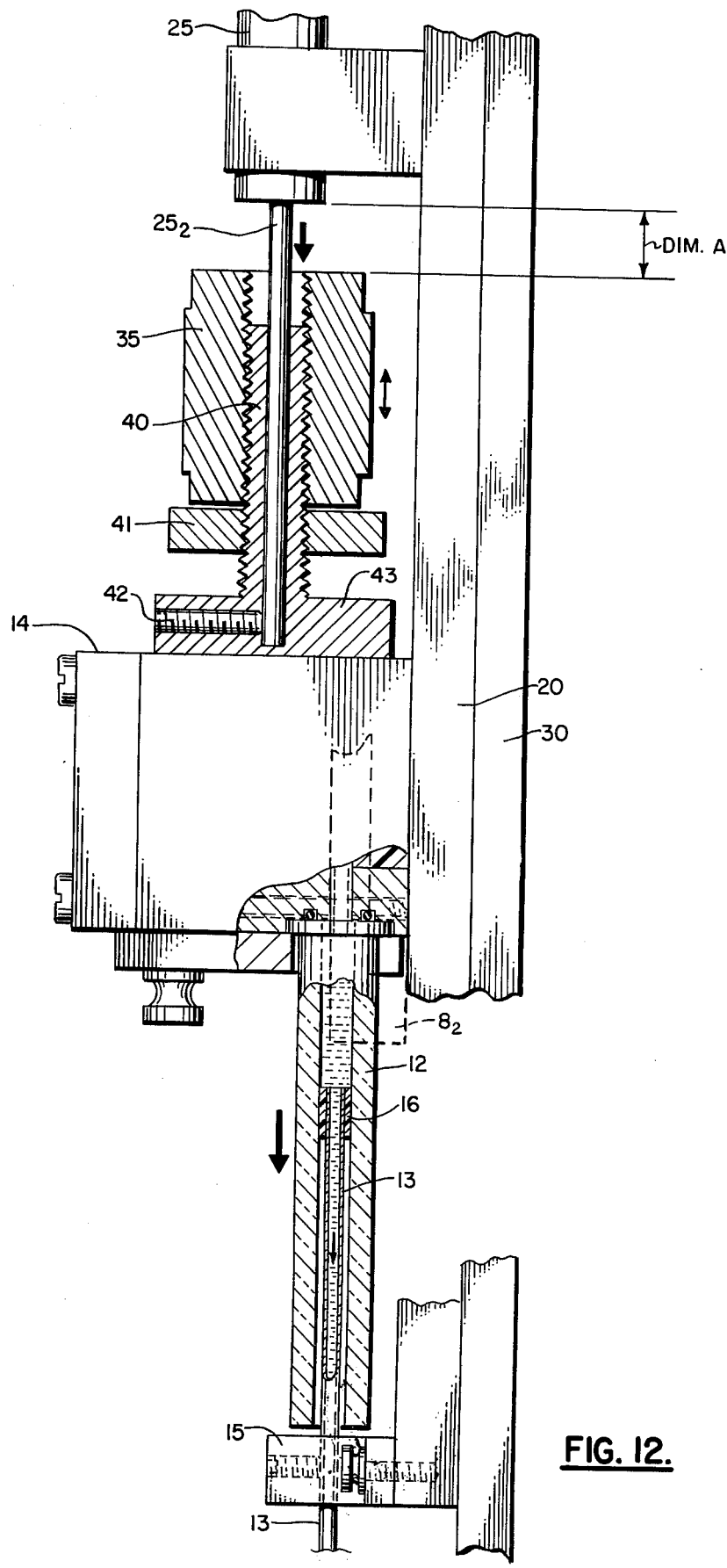

FIG. 12 details further an important portion of the fluid injector sub-assembly and, in particular, illustrates a preferred adjustment assembly for delivery of a preselected quantity of a fluid specimen.

Referring to the figures, initially to FIGS. 1 through 4, there is described a preferred type of automatic fluid injector 100. The principle components of the automatic fluid injector 100 include generally (a) a fluid injector sub-assembly 10, inclusive of a fluid injector per se, comprised of a barrel 12, hollow needle or cannula 13 and valve 14, (b) an injector feed assembly 50, inclusive of a reciprocable hollow probe 51 which constitutes the primary contact device of this sub-assembly used for the pick-up of a fluid specimen, and (c) a magazine or carrousel type feed tray 90 for transporting one or a plurality of vials of fluid specimens to the injector feed assembly 50 for pick up by probe 51 for delivery to the fluid injector per se of the fluid injector sub-assembly 10. Accurately measured portions of the fluid specimens are injected into, e.g., an inlet 120 of an analytical instrument, via the direct action of the fluid injector, or fluid injector sub-assembly 10. These several sub-assemblies (a), (b) and (c) are generally contained in whole or in part within a casing, or housing 110, and responsive to automatic control means such as described in U.S.

Pat. No. 3,754,443, supra. In brief compass, the principle features and overall function of these several sub-assemblies and their relation one to another are generally as follows:

a. The fluid injector sub-assembly 10, the principle purpose of which is to arcuately measure out a preselected quantity of a fluid specimen for delivery to a media, or instrument, includes generally a fluid injector per se which is comprised of a tubular component of barrel 12, a cannula or hollow needle 13 slidably mounted within the front end of said barrel, and a valve 14. In its more preferred aspects these several components of the fluid injector, i.e., barrel 12, needle 13 and valve 14, are mounted upon a plate 20 which, in turn, is slidably mounted upon a base plate 30 which is affixed to a portion of the casing or housing 110. It is essential that the barrel 12 and needle 13 be mounted such that one member can be reciprocably moved relative to the other and therefore, suitably, the needle 13 is rigidly secured to the slide plate 20 via the needle clamp 15, comprised of a tubular section $15_1$ containing an internal tubular gland through which the needle 13 is passed and retained in place by a set screw $15_2$; the tubular section being affixed upon slide plate 20 via set screws $15_3$, $15_4$. So affixed, the needle 13 is not capable of movement relative to slide plate 20, but free relative movement of barrel 12 is permitted. Suitably, the rearward end of the needle 13 is provided with a circumferential seal 16 affixed thereon, to prevent leakage of fluid from the annulus between the needle and barrel, as barrel 12 is moved thereupon.

The valve 14 is located at the rearward end of barrel 12, between guides $8_1$, $8_2$, its function being to open and close the barrel 12 to the flow of a fluid specimen delivered thereto. When the valve 14 is open, both ingress and egress of a fluid specimen through the barrel 12 and needle 13 is permitted. When closed, the flow is interrupted, and on closure to interrupt a previously flowing stream of a fluid specimen, a sample of the fluid specimen is trapped within the barrel 12 and needle 13, and ready for subsequent ejection through the dispensing end $13_1$ of the needle.

Virtually any valve which can be controlled in response to a signal, particularly an electrical signal, to provide an on and off position can be employed. Suitably, the valve employed is an electrically controlled fluid actuated valve 14, e.g., a single acting fluid actuatable piston unit. Referring for convenience to FIGS. 8 and 9, the valve 14 is comprised of a body, or block $14_1$, which is provided with a pair of tubular openings $14_2$, $14_3$ communicated one with the other via a central channel $14_4$. The tubular opening $14_3$ is provided with a tubular packing 17, the axial opening $17_1$ of which is communicated with a tubular segment 18 inserted therein, and held in place via a lock screw 19. A lateral opening $17_2$ which enters into the axial opening $17_1$ of packing 17 is connected with a tubular segment 21 which enters into the rear of barrel 12. The tubular opening $14_2$ is closed at the top by a plate $14_5$ held in place by screws $14_{6A}$, $14_{6B}$, $14_{6C}$ and $14_{6D}$ which secures said top to the valve body $14_1$, and holds the valve 14 in place on the slide plate 20. A piston 22, inclusive of a head $22_1$ and stem $22_2$ provides the closure element for the valve. The head $22_1$, with its circumferential O-rings $22_{1A}$, $22_{1B}$ is snugly fitted within the tubular opening, the stem $22_2$ extending into the communicating channel or opening $14_4$ and entering partially into the axial opening $17_1$ of tubular packing 17. The head $22_1$ of the piston is biased in closed position (FIG. 9) by a spiral spring $22_3$ which is seated between the inner face of valve top plate $14_5$ and the outer face of head $22_1$ of the piston 22. The function of this valve will be quite clear by continued reference to FIGS. 8 and 9. With reference to FIG. 8, on entry of a pressurized gas, e.g., air or nitrogen, into the valve body via opening 24, located within channel $14_4$, the pressure exerted by the helical spring $22_3$ is overcome and the valve is opened by withdrawal of the stem $22_2$ from the junction between openings $17_1$, $17_2$ and a fluid specimen can ingress through these openings to fill the barrel 12 and needle 13. Conversely, when no pressurized gas is admitted through the opening 24, the helical spring $22_3$ causes extension of stem $22_2$ into the junction formed by openings $17_1$, $17_2$, thus closing off the flow of fluid specimen into the barrel 12 and needle 13 (FIG. 9).

The fluid injector sub-assembly 10 also includes means for actuating and reciprocating the barrel 12, suitably drive means which can be actuated and controlled in response to a signal, especially on electrical signal. Such means is, suitably, a piston, particularly a fluid actuatable double acting piston unit 25 mounted on slide plate 20. The piston unit 25, as shown e.g. in FIGS. 10 and 11, is comprised of an outer cylinder $25_1$ with its piston, inclusive of rod $25_2$ and head (not shown). The end of piston rod $25_2$ is secured to the barrel 12 via attachment to an adjustment assembly mechanism 35 located at the rear of valve 14 which forms an integral part of the barrel assembly. Reciprocation of the piston rod $25_2$ produces reciprocal movement of barrel 12, without corresponding movement of the needle 13. Such reciprocation of the piston rod $25_2$ is, of course, produced by alternate injections of a pressurized fluid, e.g., a gas such as air or nitrogen, via lines $26_1$ and $26_2$; the piston rod $25_2$ being moved downwardly when pressurized gas is injected into the piston unit 25 via line $26_1$ (gas being simultaneously expelled via line $26_2$) and upwardly when pressurized gas is injected into the piston unit 25 via line $26_2$ (gas being simultaneously expelled via line $26_1$).

A drive means for actuating and reciprocating the entire fluid injector sub-assembly 10 is also required. In its preferred aspects, the slide plate 20 is slidably mounted upon the base plate 30 via means of a guide slot (not shown) cut through the base plate 30, the slide plate 20 riding therein and being retained in such position via means of a bolt (not shown) with an enlarged head (larger than the width of the slot) which is screwed or otherwise secured upon slide plate 20 with its head projected on the opposite side of the guide slot to hold the plates 20, 30 together. A plastic retention member, or bracket 31 of L-shaped cross-section, bolted upon plate 30, also aids in holding plates 20, 30 together, plate 20 being slidably mounted in relation to bracket 31 and plate 30. A fluid actuatable piston unit 27 is mounted on the base plate 30, and it is operatively associated with slide plate 20, its function being to reciprocate the entire slide plate 20 along a guided path for insertion (and withdrawal) of the dispensing end $13_1$ of needle 13 into a suitable media, e.g., a septum inlet 120 of an analytical instrument, into which a preselected accurately measured quantity of a fluid specimen is to be injected. Referring, e.g., to FIGS. 10 and 11, it will thus be observed that the piston unit 27, like piston unit $25_1$ is also comprised of a cylinder $27_1$ with its piston, inclusive of rod $27_2$ and head (not shown). The rod $27_2$ of piston unit 27 is attached via a mounting bracket 28 to the slide 20 such that pressurized gas injected via line $29_1$ into the upper end of the piston unit causes movement of the slide plate 20 downwardly to thrust needle 13 into inlet 120 (while gas is expelled from line $29_2$), and gas injected via line $29_2$ into the lower end of the piston unit 27 causes movement of the slide plate 20 upwardly to withdraw needle 13 from inlet 120 (while gas is expelled from line $29_1$).

Means are also provided for adjusting the relative distance of movement between the needle 13 and barrel 12 of the fluid injector sub-assembly 10, such that the rearward end of needle 13 will move only a preset distance into the barrel 12 in the displacement of a preselected volume of fluid specimen therefrom. Whereas various means for accomplishing this are feasible, a preferred adjustment assembly 35 forms an integral part of the fluid injector sub-assembly 10. Referring to FIG. 12, the preferred adjustment assembly 35 is mounted rearwardly of valve 14 and affixed upon the forward end of piston rod $25_2$ of piston unit 25. Thus, it will be observed that a cylindrical shaped member 43, provided with an externally threaded tubular projection 40, abutts with and is affixed to the rearward (or upwardly faced side) of valve 14. The forward terminal end of piston rod $25_2$ is extended through the opening through the externally threaded tubular projection 40, held in place and affixed to the adjustment assembly 35 via the set screw 42. The volume set knob 35 is of tubular design, internally threaded, and threadably engaged with the externally threaded projection 40. By rotation of the volume set knob 35 in one direction it is moved, e.g., upwardly on externally threaded projection 40. Conversely, by rotation in the opposite direction, the volume set knob 35 is moved downwardly. It is conveniently locked and retained at a desired level by the lock ring 41. The linear distance of movement of the plunger 12 is set by adjusting the distance between the upward face of volume set knob 35 and the lower face of the cylinder of piston unit 25, and this is accomplished by mere rotation of volume set knob 35 to move said knob upwardly or downwardly upon the externally threaded projection 40. Dimension A, i.e., "Dim. A," as shown in the figure thus corresponds to the distance of movement of barrel 12, which in turn corresponds with the distance that needle 13 moves inside the barrel 12. Accordingly, the volume is fluid displaced and can be easily predetermined, and set by means of the adjustment assembly 35.

A novel fluidic diversion valve 70, the details of which are best shown by reference to FIG. 8, also constitutes a part of the overall fluid injector sub-assembly 10. The purpose of this valve 70 is to collect and transfer the fluid specimen ejected from barrel 12 and needle 13 as occurs during the cleaning, purging and filling step. Referring specifically to FIG. 8, it will be observed that the fluidic diversion valve 70 is constituted as a generally tubular member, preferably formed of a resilient plastic or plastic-like material, suitably a self-sealing semi-rigid or rigid plastic such as polytetrafluoroethylene (Teflon) within which is contained, besides the axial opening $70_1$, at least one and suitably a pair of lateral inlet openings $71_1$, $71_2$ and at least one, suitably one lateral outlet opening $71_3$. The openings $71_1$, $71_2$ and $71_3$ are of at least equal, but pfeferably larger diameter than axial opening $70_1$, such that when a gas, e.g., air or nitrogen, is introduced into inlets $71_1$, $71_2$ the gas will sweep out the annulus between the external needle wall and inside wall of the axial opening $70_1$ and convey fluid specimen through the outlet opening $71_3$ and via the tubing 73 to the flush bottle 74. In a particularly preferred embodiment a seal is formed within the openings $71_1$, $71_2$ by a pronged metal member $70_2$ (FIG. 2) to which a flexible tubing 72 is connected to convey gas into said annulus, and a second seal is formed in the outlet side by a tubular metal segment $70_3$ to which the flexible hose 73 is adjoined.

b. The function of the injector feed assembly 50 is to provide a fluid specimen, which it obtains from a vial delivered by magazine 90, for filling the barrel 12 and needle 13 of the fluid injector sub-assembly 10. The injector feed assembly 50 is comprised of means, suitably a double acting piston unit 55, the piston rod of which is integral or associated with a reciprocable hollow probe, or pair of probes, 51. These and other components of the probe assembly enable said probe 51 to be projected into a vial via action of the piston unit 55, the probe 51 acting as a means of pressurizing the contents of the vial and as a conduit for receipt and transfer of the fluid specimen via the probe 51 to the barrel 12 of feed injector sub-assembly 10.

Referring, e.g., to FIGS. 1 and 3–6, and 7 for convenience, the principal parts of the injector feed assembly 50 include a piston unit 55 mounted upon a portion of the casing or housing 110, and probe assembly 51 (FIG. 7). The piston unit 55 is comprised of an outer cylinder $55_1$, with its included piston, inclusive of rod $55_2$ and head (not shown). The rod $55_2$ is reciprocated by alternate injection of a pressurized fluid, e.g., a gas such as air or nitrogen, into the cylinder $55_1$ via line $55_3$ to cause withdrawal of the piston rod $55_2$ (gas being simultaneously expelled via line $55_4$) or into cylinder $55_1$ via line $55_4$ to cause extension of the piston rod $55_2$ (gas being simultaneously expelled via line $55_4$). For compactness in the construction of the instrument, the probe assembly 51 and piston unit 55 are mounted such that the motion of the piston rod $55_2$, which acts upon and reciprocates the probe 51 in a substantially vertical plane, lie in different planes. This is accomplished by means of a yoke 56 having a diagonal slot (or 45° from horizontal) which is mounted on the terminal end of rod $55_2$, the slotted portion of said yoke 56 being mated with a pin 57 located on the probe assembly 51 which rides within a vertical slot provided within a bracket 58 affixed upon the casing or housing 110. The force of the reciprocating piston rod $55_2$ is thus redirected, an outward thrust of the piston rod $55_2$ being translated into a downward thrust upon the probe assembly 51 to cause its descent, a withdrawal of the piston rod $55_2$ into cylinder $55_1$ being translated into an upward thrust upon the probe assembly 51 causing its ascent.

A preferred type of probe assembly 51 is shown by specific reference to FIG. 7, the probe portion thereof being shown projected into a vial 60 which contains a fluid specimen which is to be delivered to the fluid injector subassembly 10. The probe per se is constituted of a pair of hollow needles $51_1$, $51_2$ concentrically mounted, an inner needle $51_2$ contained within a larger diameter outer needle $51_1$. An annulus between the inner needle $51_2$ and outer needle $51_1$ provides an internal conduit within which a pressurized gas, e.g., air or nitrogen, can be transmitted through an inlet as via a connecting tube 59, the gas entering vial 60 via the opening or exit port $51_3$. Since the gas cannot escape through the septum $60_1$, which is tightly held on top of the vial by the screw cover $60_2$, the fluid contents of the vial are pressurized by the entering gas, and the fluid specimen is forced into the entry port $51_4$, the fluid specimen ascending through the bore of needle $51_2$ and exiting via the connecting tubing 61.

c. The magazine 90, or feed tray, whose chief function it is to transport a fluid specimen filled vial, or vials, to a location for pick-up by the probe, or probe assembly 51, can be one of several types as described in application Ser. No. 618,374, U.S. Pat. No. 3,754,443, U.S Pat. No. 3,824,859, U.S. Pat. No. 3,885,438, U.S. Pat. No. 3,940,995, or the like, supra. In a preferred embodiment, as described herein, a carrousel feed tray or magazine 90 is provided for conveying fluid specimen containing vials 60 in seriatim to a location beneath the probe assembly 51 for pick up. The vials 60, as suggested by reference to FIG. 7, are suitably of an open screw top type, sealed with an elastometer septum $60_1$ to prevent leakage and contamination, and permit pressurization. As the vials 60 are moved into position beneath the probe assembly 51, the probe 51 is thrust downwardly under the influence of piston unit 55, the pointed or tapered end thereof passing through the open cap $60_2$ to penetrate the septum $60_1$ of the vial for pick-up and delivery of the fluid specimen.

An operating cycle is described by reference to the figures, particularly to FIGS. 5 through 12, these figures depicting a series of views describing the cleaning and purging, filling and injection of an accurately measured fluid specimen obtained from a vial delivered by the magazine or feed tray. The cycle can be repeated in timed sequence ad infinitum, as follows:

a. Referring initially to FIG. 5, a cleaning and purging portion of an operating cycle is described. The injector feed sub-assembly 50 is activated by injection of pressurized gas via line $55_4$ into piston unit 55 causing outward thrust of piston rod $55_2$, the probe assembly 51 being cammed downwardly by action of slotted yoke 56 acting against the pin 57 which rides within the vertical slot of bracket 58. The septum $60_1$ (FIG. 7) of the gastight vial 60 is penetrated by the sharp, pointed end of probe 51 which is moved into the vial 60 until port $51_4$ is submerged in the liquid, and port $51_3$ is within the vapor spore between the surface of the liquid and the septum $60_1$. Pressurized gas injected via line 59 into the annulus between needles $51_1$, $51_2$ enters into the vial 60 via port $51_3$ effectively pressurizing the vial, thus causing fluid specimen contents to enter into port $51_4$, ascend thrugh the bore of the needle $51_2$, and exit via tubing 61. The fluid specimen is conveyed via the tubing 61 to the valve 14 which, at this point in time, is in open position (FIG. 8), the valve having been opened and retained in open position by pressurized gas injected via line 9 through the port 24.

Fluid specimen is passed through line 61, inlet 18 and openings $17_1$, $17_2$ into the rear of barrel 12. The fluid passes through the rearward end of said barrel 12 and then through the bore of needle 13, the flowing stream of fluid cleaning and purging the barrel 12 and needle 13 of any contamination as, e.g., may be present from a previous injection with a different fluid specimen.

Continuing for convenience to refer to FIG. 8, the needle 13 of the fluid injector sub-assembly 10 is shown in a position of withdrawal from the septum inlet 120, the dispensing end $13_1$ thereof being located within the fluidic diversion valve 70. A gas, e.g., air or nitrogen, is passed through the dual opening $71_1$, $71_2$ via line 72, and around the annulus within which the needle is contained to sweep fluid specimen from the needle 13 through outlet opening $71_3$. The excess liquid is conveyed via line 73 to flush bottle 74 (FIG. 6).

b. To close the valve 14, and complete the cleaning and purging step of the sequence the flow of pressurized gas to the valve 14 via opening 24 is ceased, this releasing the tension on helical spring $22_3$. As this occurs, the helical spring $22_3$ (formerly under tension as depicted in FIG. 8) urges the piston head $22_1$ inward (FIG. 9), the piston rod $22_2$ being thrust past the junction of axial opening $17_1$ and lateral opening $17_2$ thus cutting off the flow of fluid specimen via line 61 into linet 18, and openings $17_1$, $17_2$ at the rearward end of barrel 12. In interrupting the flow in this manner, an uncontaminated portion of the fluid specimen is trapped within the barrel 12 and needle 13 of the fluid injector sub-assembly 10.

c. The purging, cleaning and filling function of injector feed assembly 50 now having been completed, the probe 51 can at this time be withdrawn from vial 60 and repositioned for use in the subsequent cycle as depicted, e.g., by reference to FIG. 1. Withdrawal of the probe 51 is accomplished by injection of pressurized gas via line $55_3$ into piston unit 55 (gas being expelled via line $55_4$). Such action, not specifically detailed, is readily apparent by reference to FIG. 5 which can be read with all of the black arrows reversed. In other words, piston rod $55_2$ would be withdrawn, and the slotted yoke 56 would cause the probe 51 to be cammed upwardly to withdraw same from the vial 60. A new vial is then introduced into position by magazine 90 (FIG. 3) for pick-up by the probe assembly 51 in the next cycle of operation.

d. To initiate the sequence required for the actual injection of the fluid specimen, the fluid injector sub-assembly 10, inclusive of barrel 12, needle 13, valve 14 and piston 25, carried on slide plate 20 is moved downwardly by transport or movement of slide plate 20. Referring initially to FIG. 10, pressurized gas is injected via line $29_1$ into piston unit 27 this causing piston rod $27_2$ to be thrust outwardly or downwardly (as gas is expelled from the opposite side of the piston unit 27 via line $29_2$). Outward thrust of piston rod $27_2$ carries the slide plate 20 downwardly, and thrusts the needle 13 deeply into septum inlet 120 of an analytical instrument, e.g., a gas chromatograph.

e. The actual injection step is shown by reference to FIGS. 11 and 12. Actual injection is accomplished by means of the piston unit 25. Pressurized gas is injected via line $26_1$ into the rearward end of the unit, this causing extension of piston rod $25_2$ (while gas is simultaneously expelled via line $26_2$). On extension of the piston rod $25_2$ the adjustment assembly 35, valve 14 and barrel 12 are thrust downwardly while the needle 13 is held in fixed position. As this occurs, the barrel 12 is moved relative to the needle 13 and the rearward end of the latter is thrust inwardly into the barrel 12 to displace fluid specimen from the dispensing end $13_1$ of the needle 13. As this occurs, the so-ejected fluid specimen is injected into the septum inlet 120 and conveyed into the instrument via carrier gas introduced at line 121. By specific reference to FIG. 12 it is quite evident that the volume of fluid specimen actually injected is equal to the volume of fluid specimen displaced by the needle on its displacement into the barrel 12.

f. After injection of the fluid specimen the barrel 12 of the fluid injector sub-assembly 10 is repositioned in relation to needle 13, as prior to initiation of step (e) wherein the barrel 12 was slid over the rear end of the needle 13 to eject the fluid specimen. This is accomplished by injecting pressurized gas via line $26_2$ to cause the withdrawal of piston rod $25_2$ of piston unit 25 (with the simultaneous expelling of gas via line $26_1$) which moves the barrel 12, valve 14 and adjustment assembly rearwardly while the needle 13 is held in fixed relative position.

g. The slide 20 is then repositioned, and needle 13 withdrawn from the septum inlet 120 by injection of pressurized gas via line $29_2$ into the front end of piston unit 27 (while gas is expelled via line $29_1$). (At this point in time this probe assembly 51 could be repositioned, and a fresh via delivered by magazine 90 for pick-up in lieu of such step having been previously conducted as in step (c).)

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the fluid injector is normally constructed of glass, but can be constructed of a plastic or plastic-like material. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or elastic-like materials, such as natural or synthetic rubbers can also be employed.

The fluid injector sub-assembly (except for the barrel), the injector feed assembly, particularly the needle and probes, the piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode or particular sequence of withdrawing or delivering fluids, can be made without departing the spirit and scope of the invention, as will be apparent to those skilled in this art.

Having described the invention, what is claimed is:

1. A fluid injector for the measurement and injection of preselected quantities of a fluid specimen into a media such as an inlet to an analytical instrument which comprises
   a barrel,
   a hollow needle sealed and slidably mounted within the forward end of said barrel,
   a valve located at the rearward end of said barrel for opening and closing said barrel to the flow of the fluid specimen through the barrel and hollow needle,
   whereby, on opening the valve, the fluid specimen can be flowed through the barrel and needle to purge and clean same and, on closing the valve, a measured amount of the fluid specimen can be trapped inside the barrel and needle, and then injected by relative forward movement of the barrel such that the needle moves rearwardly into the barrel to displace and cause ejection of the fluid specimen through the forward end of the hollow needle.

2. A fluid injector for the measurement and injection of preselected quantities of fluid specimens into a media such as an inlet to an analytical instrument which comprises
   a fluid injector sub-assembly inclusive of
   a barrel,
   a hollow needle sealed and slidably mounted within the forward end of said barrel,
   a valve located at the rearward end of said barrel for opening and closing said barrel to the flow of fluid specimen through the barrel and hollow needle,
   a plate upon which said fluid injector sub-assembly is mounted and to which the hollow needle of the fluid injector sub-assembly is rigidly affixed,
   means associated with said fluid injector sub-assembly for movement of said assembly along a predetermined path for insertion of the needle thereof into the inlet of the analytical instrument, and
   means associated with the barrel of said fluid injector sub-assembly for movement of same relative to the hollow needle,
   whereby, on opening the valve of the fluid injector sub-assembly, the fluid specimen can be flowed through the barrel and needle to effectively purge and clean these members and, on closing the valve, a measured amount of fluid specimen can be trapped inside the barrel and needle, and then on insertion of the needle into the inlet of the analytical instrument, the fluid specimen can be injected by the relative forward movement of the barrel such that the needle moves rearwardly into the barrel to displace and cause ejection of the fluid specimen through the forward end of the needle and into the inlet.

3. The apparatus of claim 2 wherein the plate is slidably mounted upon a base plate, and said sidable plate is associated with, actuated and movable by a piston unit which constitutes the associated means for movement of said fluid injector sub-assembly along the predetermined path.

4. The apparatus of claim 2 wherein the plate is slidably mounted upon a base plate, said slidable plate is associated with, actuated and movable by a first piston unit which constitutes the associated means for movement of said fluid injector sub-assembly along the predetermined path, the valve is opened and closed by means of a stem actuatable by a second piston unit, the barrel and valve portions of the fluid injector sub-assembly is movable by means of a third piston unit, and both the second and third piston units are mounted upon the slidable plate.

5. A fluid injector for the measurement and injection of preselected quantities of fluid specimens into a media such as an inlet to an analytical instrument which comprises
   a fluid injector sub-assembly inclusive of
   a barrel,
   a hollow needle sealed and slidably mounted within the forward end of said barrel,
   a valve located at the rearward end of said barrel for opening and closing said barrel to the flow of fluid specimen through the barrel and hollow needle, a slide plate upon which said fluid injector subassembly is mounted and to which the hollow needle of the fluid injector sub-assembly is rigidly affixed, a base plate, which can constitute a portion of housing of said fluid injector, upon which said slide plate is slidably mounted, means mounted upon said base plate associated with said slide plate for producing the movement of said slide plate and fluid injector sub-assembly carried thereon along a predetermined path for insertion of the needle of the fluid injector sub-assembly into the inlet of the analytical instrument, means associated with the barrel of said fluid injector assembly for producing movement of said barrel relative to the needle of the fluid injector sub-assembly, an injector feed sub-assembly inclusive of a probe assembly constituted of one or a pair of hollow probes provided with communicating upper and lower openings mounted adjacent to said base plate in a generally vertical plane of orientation, including means for actuation and reciprocation of said probes, and means for transfer of a pressurized medium through a hollow probe, and a feed tray for transporting a fluid specimen contained in a vial, with a resilient, puncturable closure, into the path of a hollow probe for penetration of said closure by the probe whereby, on penetration of the puncturable closure of a vial by a probe, a pressurized fluid can be injected through the probe into the vial to pressurize the fluid specimen contained therein, the fluid specimen then transferred, when the valve of the fluid injector sub-assembly is open, from the vial via a hollow probe to the opening within said barrel, flowed through the barrel and needle to effectively clean these members and, on closing the valve, a measured amount of the fluid specimen can be trapped inside the barrel and needle, and then on thrust of the needle of the fluid injector sub-assembly into said inlet to the analytical instrument via activation of the means which produces movement of the slide plate, the fluid specimen can be injected by the relative forward movement of the barrel such that the needle moves rearwardly into the barrel to displace and cause ejection of the fluid specimen through the forward end of the needle and into the inlet of the analytical instrument.

6. The apparatus of claim 5 wherein the slide plate is activated by a first piston unit, the valve is opened and closed by means of a stem actuatable by a second piston unit mounted on the slide plate, and the barrel and valve portions of the fluid injector sub-assembly is movable by means of a third piston unit mounted on the slide plate.

7. The apparatus of claim 5 wherein the fluid injector sub-assembly also includes means for adjusting the relative distance of movement between the hollow needle and barrel of the fluid injector sub-assembly, such that the rearward end of the needle moves a preselected distance into the barrel in ejecting fluid specimen from the barrel.

8. The apparatus of claim 5 wherein the fluid injector sub-assembly inclusive of barrel, hollow needle sealed and slidably mounted within the forward end of said barrel, valve located at the rearward end of said barrel for opening and closing said barrel to the flow of fluid specimen through the barrel and hollow needle, and means for adjusting the relative distance of movement between the hollow needle and barrel of the fluid injector sub-assembly, such that the rearward end of the needle moves a preselected distance into the barrel in ejecting fluid specimen from the barrel is comprised of an externally-threaded tubular member, an end of which is affixed to the valve of the injector sub-assembly and to said means associated with the barrel for producing movement of said barrel relative to the needle of said fluid injector sub-assembly, and an internally threaded tubular knob mounted upon and threadably engaged with said externally threaded tubular knob whereby rotation of said knob in one direction lengthens the relative distance of movement between the hollow needle and barrel, and rotation of said knob in the opposite direction shortens the relative distance of movement between the hollow needle and barrel.

9. The apparatus of claim 8 wherein the combination includes a fluidic diversion valve constituted of a tubular member, formed by a wall surrounding an axial opening of internal diameter larger than the external diameter of the needle which, when fitted therein, provides an annular opening surrounding said needle, and a lateral opening extending through the wall and said axial opening, whereby fluid can be passed through the lateral opening to sweep and clean the annulus between the external wall of the needle and internal wall of the axial opening of the fluidic diversion valve.

10. The apparatus of claim 9 wherein the lateral opening of the fluidic diversion valve includes a pair of inlet openings, and a single outlet opening, these openings being of greater diameter than the diameter of the axial opening.

* * * * *